United States Patent
Laitala

(10) Patent No.: US 10,222,330 B2
(45) Date of Patent: Mar. 5, 2019

(54) DEVICE AND A METHOD FOR DETECTING A SAMPLE CONTAINED BY A SAMPLE WELL

(71) Applicant: WALLAC OY, Turku (FI)

(72) Inventor: Ville Petteri Laitala, Turku (FI)

(73) Assignee: WALLAC OY, Turku (FI)

( * ) Notice: Subject to any disclaimer, the term of this patent is extended or adjusted under 35 U.S.C. 154(b) by 0 days.

(21) Appl. No.: 15/322,177

(22) PCT Filed: Jun. 15, 2015

(86) PCT No.: PCT/FI2015/050426
§ 371 (c)(1),
(2) Date: Dec. 27, 2016

(87) PCT Pub. No.: WO2015/197912
PCT Pub. Date: Dec. 30, 2015

(65) Prior Publication Data
US 2017/0153183 A1    Jun. 1, 2017

Related U.S. Application Data

(60) Provisional application No. 62/017,927, filed on Jun. 27, 2014.

(30) Foreign Application Priority Data

Jun. 27, 2014    (FI) .................................. 20145624

(51) Int. Cl.
*G01N 21/64*    (2006.01)

(52) U.S. Cl.
CPC ..... *G01N 21/6408* (2013.01); *G01N 21/6452* (2013.01)

(58) Field of Classification Search
CPC ............... G01N 21/64; G01N 21/6452; G01N 21/6486; G01N 21/6408
See application file for complete search history.

(56) References Cited

U.S. PATENT DOCUMENTS

2005/0046849 A1    3/2005  Cromwell et al.
2006/0147954 A1    7/2006  Laitala et al.
(Continued)

FOREIGN PATENT DOCUMENTS

CN    103649728         3/2014
EP    2 485 040 A1      8/2012
(Continued)

OTHER PUBLICATIONS

Finnish Search Report, dated Jan. 29, 2015, from corresponding Finnish application.
(Continued)

*Primary Examiner* — David P Porta
*Assistant Examiner* — Faye Boosalis
(74) *Attorney, Agent, or Firm* — Young & Thompson

(57) ABSTRACT

A device for detecting whether a sample well (352) contains a sample is presented. The sample well contains one or more fluorescent substances needed for an optical analysis of the sample. The device includes a controller (312) configured to compute, on the basis of a luminescence, e.g. fluorescence, emission signal measured from the sample well, an indicator value indicative of a decay time of the measured fluorescence emission signal. The controller is configured to compare the indicator value to a reference value and to set, in accordance with the comparison, a detection result to express that the sample well contains the sample or that the sample well does not contain the sample.

18 Claims, 4 Drawing Sheets

(56) References Cited

U.S. PATENT DOCUMENTS

2011/0033872 A1  2/2011  Vaisanen et al.
2011/0034343 A1  2/2011  Erling et al.

FOREIGN PATENT DOCUMENTS

EP    2 685 260 A1   1/2014
WO   2013-012656    1/2013

OTHER PUBLICATIONS

International Search Report, dated Sep. 28, 2015, from corresponding PCT application.
Wolfgang Becker et al., "Lifetime Imaging Techniques for Optical Microscopy", Feb. 2003, retrieved from the Internet: http://www.becker-hickl.de/pdf/tcvgbh1.pdf.
Ville Laitala et al., "Time-resolved detection probe for homogeneous nucleic acid analyses in one-step format", Analytical Biochemistry, 2007, pp. 126-131, vol. 361.

DEVICE AND A METHOD FOR DETECTING A SAMPLE CONTAINED BY A SAMPLE WELL

FIELD OF THE DISCLOSURE

The disclosure of this document relates generally to managing samples to be analyzed. More particularly the disclosure relates to a device for detecting whether a sample well contains a sample. The device can be, for example but not necessary, a part of an optical measurement instrument. Furthermore, the disclosure relates to a method and to a computer program for detecting whether a sample well contains a sample. Furthermore, the disclosure relates to an optical measurement instrument.

BACKGROUND

One conventional practice is to impregnate one or more drops of fluid samples to be analyzed onto a solid sample carrier, dry the solid sample carrier impregnated with the fluid, and then send the solid sample carrier to a laboratory for analysis. The fluid to be analyzed can be, for example, blood of a newborn baby and the solid sample carrier can be, for example, a sheet of filter paper or some other suitable material which is able to carry the fluid to be analyzed. In the laboratory, one or more pieces containing the dried fluid to be analyzed are cut off from the solid sample carrier and the one or more pieces that have been cut off are conveyed, for further analysis, to one or more sample wells of e.g. a microtitration plate or some other sample well element. Each piece can be cut off from the solid sample carrier for example with a punch and a die provided with a channel for the punch, where the punch is arranged to cut off the piece with a single stroke through the solid sample carrier. It is also possible to use a cutting instrument capable of producing a localized, point-form cut on the solid sample carrier and to move the point-form cutting impact produced by the cutting instrument along the outer periphery of each piece so as to detach the piece from the solid sample carrier. Another conventional practice is to handle the sample to be analyzed in liquid form so that the sample is blended or dissolved in sample carrier liquid. In this case, one or more drops of the sample carrier liquid containing the sample are dispensed to one or more sample wells for further analysis.

The analysis of a sample contained by a sample well can be based on for example labeled analyte-specific tracer molecules where concentrations of one or more analytes in the sample can be detected on the basis of changes taking place in luminescence, e.g. fluorescence, emission signals measurable from the sample well. Analysis methods of the kind mentioned above are for example methods based on the fluorescence resonance energy transfer "FRET". Details about exemplifying FRET-based analysis methods can be found for example from publications US20060147954 and V. Laitala et al., Time-resolved detection probe for homogeneous nucleic acid analyses in one-step format, Analytical Biochemistry 361 (2007) 126-131.

Prior to carrying out an analysis of the kind mentioned above, it is important to ensure that a sample is present in a sample well. The absence of the sample may cause an erroneous negative or positive result. A known method for detecting whether a sample well contains a sample is based on light absorbance caused by a piece of a solid sample carrier or substances dissolved from the piece to reagents in the sample well. An inherent limitation of the method based on the absorbance is the need to use a transparent microtitration plate or other sample well element. In many cases there is, however, a need to use or it may be advantageous to use a light impervious microtitration plate or other sample well element. In these cases, the above-mentioned method is not applicable or at least some advantages are lost. Another known method for detecting whether a sample well contains a sample is based on luminescence intensity which is dependent on the presence of the sample and/or a piece of a solid sample carrier and/or substances dissolved from the piece to reagents in the sample well. In conjunction with some analysis methods, the use of the method based on the luminescence intensity may be challenging because the effect of the sample and/or the sample carrier on the luminescence intensity may be case specific and/or non-deterministic.

In the context of this document the term "solid" means that material under consideration is in none of the following phases: gas, plasma, and liquid.

In the context of this document, the term "solid" does not exclude porousness and other kind of ability to be impregnated with liquid. Therefore, in the context of this document, solid material can be porous or otherwise capable of being impregnated with liquid. Furthermore, the term "solid" does not exclude plasticity, elasticity, and flexibility of material under consideration. Yet furthermore, the term "solid" does not exclude mosaic structure of an object under consideration.

In the context of this document, the term "solid sample carrier" means a carrier made of solid material, e.g. a sheet of filter paper, capable of carrying sample material and the term "sample carrier liquid" means liquid capable of carrying sample material.

SUMMARY

The following presents a simplified summary in order to provide a basic understanding of some aspects of various exemplifying embodiments. The summary is not an extensive overview of the disclosure of this document. It is neither intended to identify key or critical elements of exemplifying embodiments nor to delineate the protection scope. The following summary merely presents some concepts in a simplified form as a prelude to a more detailed description of exemplifying embodiments.

In conjunction with the present invention, it has been surprisingly noticed the usability of the phenomenon described below. In many luminescence, e.g. fluorescence, -based analysis arrangements the decay time of a luminescence emission signal measurable from a sample well is, depending on the analysis arrangement, shorter or longer when a sample and possibly also a portion of a sampler carrier, e.g. a piece of a solid sample carrier, is/are present in the sample well than when the sample and the portion of the sampler carrier are absent. The decay time is different when there is no sample and no portion of the sample carrier in the sample well because in this case luminescence taking place in substances in the sample well is not influenced by the sample and by the possible portion of the sample carrier.

In accordance with the disclosure, there is provided a new device for detecting whether a sample well contains a sample. The device can be, for example but not necessary, a part of an optical measurement instrument. The device comprises a controller configured to:

compute, on the basis of a luminescence, e.g. fluorescence, emission signal measured from the sample well, an indicator value indicative of a decay time of the measured luminescence emission signal, compare the indicator value to a reference value, and set, in accordance with the comparison between the indicator value and the reference value, a detection result to express one of the following: (i) the sample well contains the sample, (ii) the sample is absent from the sample well.

The above-mentioned reference value can be for example a pre-determined fixed value or a value based on one or more luminescence emission signals measured from one or more reference sample wells which do not contain any samples and any portions of sample carriers but which contain other substances needed for the analysis.

It is worth noting that the above-mentioned indicator value does not necessarily have to directly indicate the decay time but it is also possible that the indicator value is an estimate of e.g. a decay rate or some other quantity or a dimensionless value which is indirectly indicative of the decay time.

In accordance with the disclosure, there is provided also a new optical measurement instrument that comprises:

a photo-detector for measuring luminescence, e.g. fluorescence, emission signal from a sample well, and a control system for controlling operation of the photo-detector.

The control system is configured to constitute a device according to the disclosure for detecting whether the sample well contains a sample.

In accordance with the disclosure, there is provided also a new method for detecting whether a sample well contains a sample. The method comprises:

computing, on the basis of a luminescence, e.g. fluorescence, emission signal measured from the sample well, an indicator value indicative of a decay time of the measured luminescence emission signal, comparing the indicator value to a reference value, and setting, in accordance with the comparison between the indicator value and the reference value, a detection result to express one of the following: (i) the sample well contains the sample, (ii) the sample is absent from the sample well.

In accordance with the disclosure, there is provided also a new computer program for detecting whether a sample well contains a sample. The computer program comprises computer executable instructions for controlling a programmable processing system to:

compute, on the basis of a luminescence, e.g. fluorescence, emission signal measured from the sample well, an indicator value indicative of a decay time of the measured luminescence emission signal, compare the indicator value to a reference value, and set, in accordance with the comparison between the indicator value and the reference value, a detection result to express one of the following: (i) the sample well contains the sample, (ii) the sample is absent from the sample well.

In accordance with the disclosure, there is provided also a new computer program product. The computer program product comprises a non-volatile computer readable medium, e.g. a compact disc "CD", encoded with a computer program according to the disclosure.

A number of exemplifying and non-limiting embodiments are described in accompanied dependent claims.

Various exemplifying and non-limiting embodiments both as to constructions and to methods of operation, together with additional objects and advantages thereof, will be best understood from the following description of specific exemplifying and non-limiting embodiments when read in connection with the accompanying drawings.

The verbs "to comprise" and "to include" are used in this document as open limitations that neither exclude nor require the existence of also un-recited features. The features recited in the accompanied dependent claims are mutually freely combinable unless otherwise explicitly stated. Furthermore, it is to be understood that the use of "a" or "an", i.e. a singular form, throughout this document does not exclude a plurality.

BRIEF DESCRIPTION OF FIGURES

Exemplifying and non-limiting embodiments and their advantages are explained in greater detail below in the sense of examples and with reference to the accompanying drawings, in which.

DESCRIPTION OF EXEMPLIFYING AND NON-LIMITING EMBODIMENTS

Figure 1:
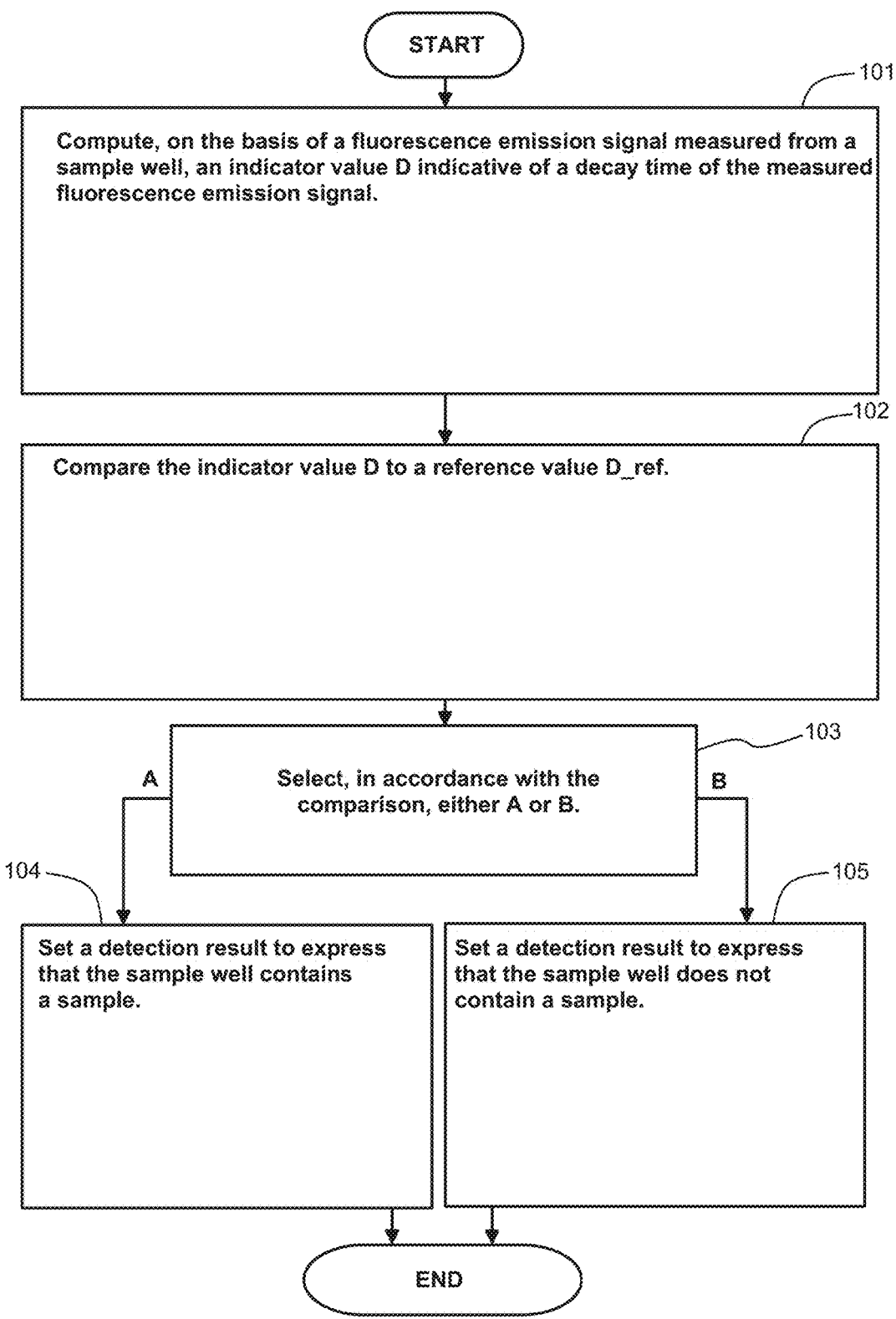
FIG. 1 shows a flowchart of a method according to an exemplifying and non-limiting embodiment for detecting whether a sample well contains a sample.

FIG. 1 shows a flowchart of a method according to an exemplifying and non-limiting embodiment for detecting whether a sample well contains a sample and possibly also a portion of a sample carrier. The sample carrier can be for example a sheet of filter paper or some other suitable solid material. It is also possible that the sample carrier is sample carrier liquid. Without limiting the generality, the sample well is assumed to contain one or more substances capable of emitting fluorescence signal after being excited by excitation radiation. The sample well may contain, for example but not necessarily, one or more populations, i.e. groups, of probes based on the fluorescence resonance energy transfer "FRET" where each probe may comprise, for example but not necessarily, at least one donor, at least one acceptor, and at least one reactive region which is capable of interacting with an analyte contained by the sample and detectable with the probe under consideration. The reactive region is capable of interacting with the analyte so that fluorescence emission of the probe is dependent on the concentration of the above-mentioned analyte.

The method illustrated in FIG. 1 comprises computing an indicator value D on the basis of the fluorescence emission signal measured from the sample well. In FIG. 1, this is illustrated by an action block 101. The indicator value D is directly or indirectly indicative of the decay time of the measured fluorescence emission signal. It is worth noting that there are many possible ways to compute the indicator value. Some exemplifying ways to compute the indicator value are described below with reference to FIG. 2 which illustrates a decaying curve of the fluorescence emission signal in different situations. The solid line curve 220 represents the decaying curve in a situation where the sample well contains the sample and the possible portion of the sample carrier, and the dashed line curve 221 represents the decaying curve in another situation where the sample well does not contain the sample and the possible portion of the sample carrier.

Figure 2:
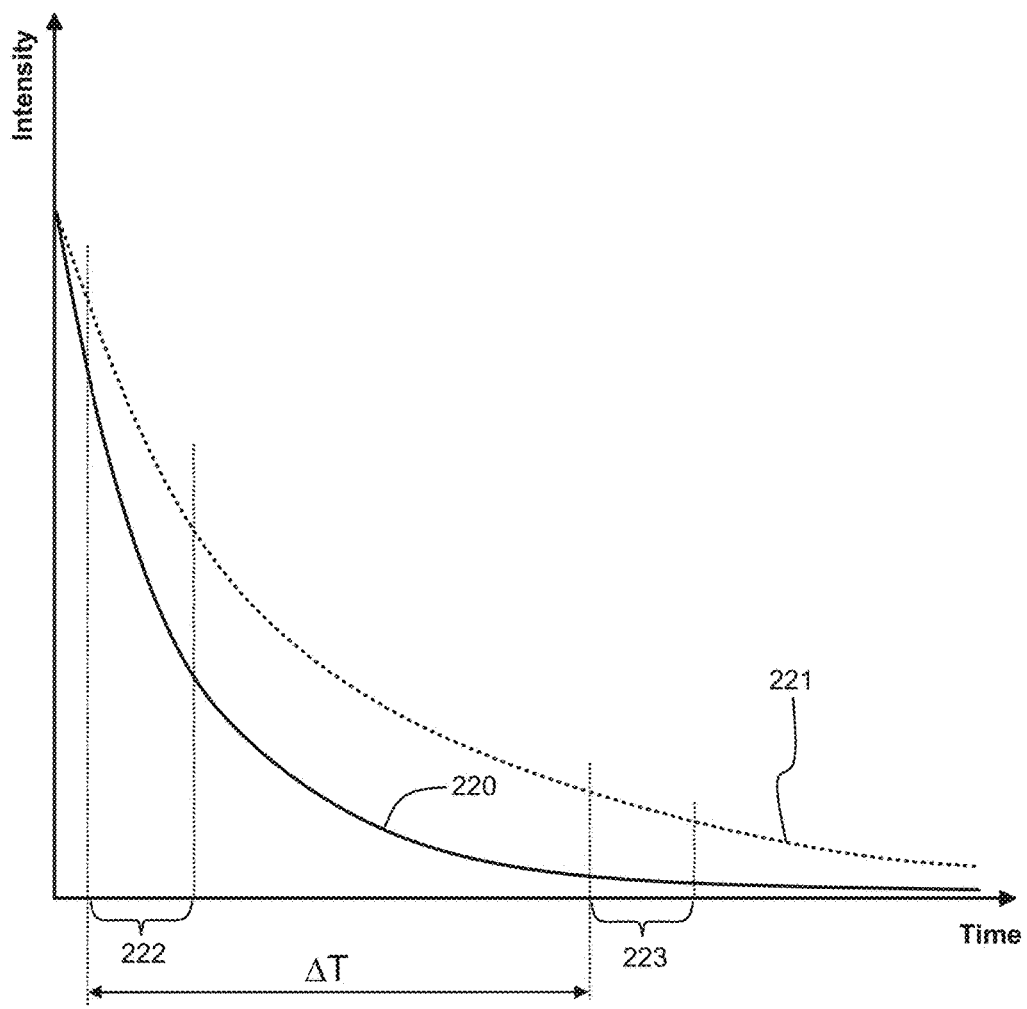
FIG. 2 illustrates decaying curves of luminescence emission signals measurable from a sample well in different exemplifying cases where a method according to an exemplifying and non-limiting embodiment is applicable.

In a method according to an exemplifying and non-limiting embodiment, the decaying curve is assumed to have the shape of a decaying exponential function both in the case where the sample well contains the sample and the possible portion of the sample carrier and also in the case where the sample well does not contain the sample and the possible portion of the sample carrier. A decaying exponential function can be presented with the following expression:

$$Ce^{-t/\tau},$$

where C is a constant, e is the Euler's number≈2.718, t is time, and τ is a decaying time constant that can be used as the indicator value D indicative of the decay time of the measured fluorescence emission signal. An estimate of the decaying time constant τ, can be computed according to the following formula:

$$\frac{\Delta T}{\ln(C_1) - \ln(C_2)}, \tag{1}$$

where ΔT is a time-shift between starting points of two measurement time windows 222 and 223 shown in FIG. 2 and having equal temporal lengths, "ln" means the natural logarithm, $C_1$ is a value proportional to strength of a signal received at a photo-detector when measuring the fluorescence emission signal from the sample well during the measurement time window 222, and $C_2$ is a value proportional to strength of a signal received at the photo-detector when measuring the fluorescence emission signal from the sample well during the measurement time window 223. The above-mentioned photo-detector can be for example a photo-multiplier tube "PMT", and the values $C_1$ and $C_2$ can be counter values indicative of amounts of photons detected during the measurement time windows 222 and 223, respectively. As can be seen from FIG. 2, the estimate of the decaying time constant τ obtained with the formula (1) is smaller for the curve 220 corresponding to the case where the sample well contains the sample and the possible portion of the sample carrier than for the curve 221 corresponding to the case where the sample well does not contain the sample and the possible portion of the sample carrier.

In a method according to an exemplifying and non-limiting embodiment, preliminary indicator values are computed according to the formula (1) for mutually different pairs of measurement time windows. The indicator value D is then computed on the basis of the preliminary indicator values. The indicator value can be for example the arithmetic mean of the preliminary indicator values. This computing method improves the accuracy of the indicator value especially in cases where the fluorescence emission signal has many components having mutually different decaying time constants.

In a method according to an exemplifying and non-limiting embodiment, the decaying curve is approximated with a straight line on a time interval from the starting point of the measurement time window 222 to the end-point of the measurement time window 223. In this case, the indicator value D can be the angular coefficient of the straight line or the inverse of the angular coefficient. For example, the inverse of the angular coefficient can be computed according to the following formula:

$$\frac{\Delta T}{C_1 - C_2}. \tag{2}$$

In a method according to an exemplifying and non-limiting embodiment, the indicator value D is computed according to the following formula:

$$\Delta T \frac{C_2}{C_1}. \tag{3}$$

The indicator value D can be obtained also with methods based on modulation of excitation radiation. The excitation radiation can be modulated for example with sinusoidal modulation and in this case the indicator signal can be computed with the aid of the amplitude and/or the phase of the alternative component of the fluorescence. Also curve fitting to measured results is possible.

The computed indicator value D is compared to a reference value D_ref in order to detect whether the decay time is shorter or longer than a limit decay time. In FIG. 1, this is illustrated by an action block 102.

In practical implementations, the above-mentioned ΔT which is the time-shift between starting points of two measurement time windows can be assumed to be same at all measurements. In this case, for example the indicator value D shown in formula (3) can be replaced with a dimensionless value $C_2/C_1$. Correspondingly, the reference value D_ref can be replaced with a corresponding dimensionless value: D_ref/ΔT. However, also in this case, the comparison between $C_2/C_1$ and D_ref/ΔT is indicative whether the decay time is shorter or longer than a limit decay time.

In exemplifying cases where the decay time is decreased due to presence of a sample and a possible portion of a sample carrier, the limit decay time is such that the sample well is deemed to contain the sample, and the possible portion of the sample carrier, when the decay time is shorter than the limit decay time, and otherwise the sample well is not deemed to contain the sample and the possible portion of the sample carrier. In cases where the indicator value D is an estimate of the decay time, the above-mentioned reference value D_ref can be the limit decay time. In cases where the indicator value D is not an estimate of the decay time but indicates the decay time indirectly, e.g. by indicating a rate of decay, the limit decay time and the reference value D_ref correspond to each other but they do not have a same value. It is worth noting that in this case there is no need to know the value of the limit decay time because the comparison is made between the indicator value D and the reference value D_ref.

In exemplifying cases where the decay time is increased due to presence of a sample and a possible portion of a sample carrier, the limit decay time is such that the sample well is deemed to contain the sample, and the possible portion of the sample carrier, when the decay time is longer than the limit decay time, and otherwise the sample well is not deemed to contain the sample and the possible portion of the sample carrier.

In a method according to an exemplifying and non-limiting embodiment, the above-mentioned reference value D_ref is a pre-determined fixed value that can be read from a memory.

A method according to another exemplifying and non-limiting embodiment comprises computing a reference indicator value RD which is directly or indirectly indicative of the decay time of a fluorescence emission signal measured from a reference sample well. The reference sample well does not contain any sample and a possible portion of a sample carrier but only other substances needed for the analysis. The reference indicator value RD is advantageously computed in the same way as the indicator value D related to the sample well under the detection operation. The reference value D_ref is then computed the basis of the reference indicator value RD. The reference value D_ref can be for example the reference indicator value RD added or subtracted with a suitable margin m, i.e. D_ref=RD+m or RD+m, or the reference indicator value multiplied with a suitable coefficient c, i.e. D_ref=c RD. For example, in cases where the indicator value D is an estimate of the decay time and the decay time is decreased due to presence of a sample and a possible portion of a sample carrier, the reference value D_ref can be RD−m where m is positive and selected so that a positive detection result is sufficiently reliable, i.e. the sample well is deemed to contain the sample and the possible portion of the sample carrier only if the decay time estimated for the sample well is with a sufficient margin shorter than the corresponding decay time estimated for the reference sample well. For another example, in cases where the indicator value D is an estimate of the rate of decay and the decay time is decreased due to presence of a sample and a possible portion of a sample carrier, the reference value D_ref can be RD+m where m is positive and selected so that a positive detection result is sufficiently reliable, i.e. the sample well is deemed to contain the sample and the possible portion of the sample carrier only if the rate of decay estimated for the sample well is with a sufficient margin greater than the corresponding rate of decay estimated for the reference sample well.

A method according to an exemplifying and non-limiting embodiment comprises computing many reference indicator values $RD_1, RD_2, \ldots, RD_N$ each being directly or indirectly indicative of the decay time of a fluorescence emission signal measured from one of N reference sample wells. Each reference indicator value is advantageously computed in the same way as the indicator value D related to the sample well under the detection operation. The reference value D_ref is then computed the basis of the reference indicator values $RD_1, RD_2, \ldots, RD_N$. The reference value D_ref can be for example an arithmetic mean of the reference indicator values added or subtracted with a suitable margin or multiplied with a suitable coefficient.

The output information of the method is a detection result which is set to express one of the following in accordance with the comparison between the indicator value D and the reference value D_ref: (i) the sample well contains the sample and the possible portion of the sample carrier, or (ii) the sample well does not contain the sample and the possible portion of the sample carrier. In FIG. 1, this is illustrated by a selection block 103 and by action blocks 104 and 105.

A computer program according to an exemplifying and non-limiting embodiment comprises computer executable instructions for controlling a programmable processing system to carry out a method according to any of the above-described exemplifying and non-limiting embodiments. The computer executable instructions can be generated with a suitable programming language.

A computer program product according to an exemplifying and non-limiting embodiment comprises a non-volatile computer readable medium, e.g. a compact disc "CD", encoded with a computer program according to an embodiment.

A signal according to an exemplifying and non-limiting embodiment is encoded to carry information defining a computer program according to an embodiment.

Figure 3A:
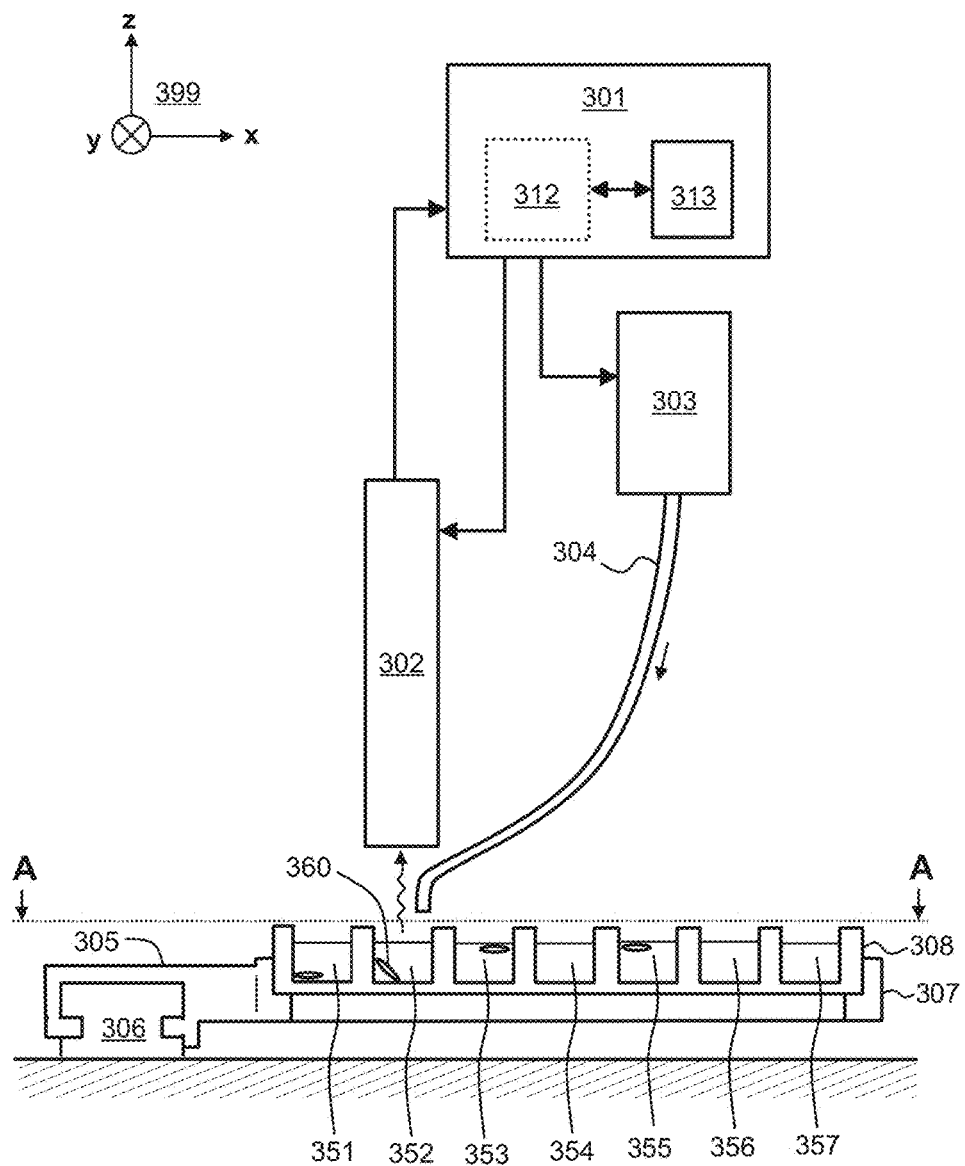
FIGS. 3a and 3b illustrate an optical measurement instrument according to an exemplifying and non-limiting embodiment.
Figure 3B:
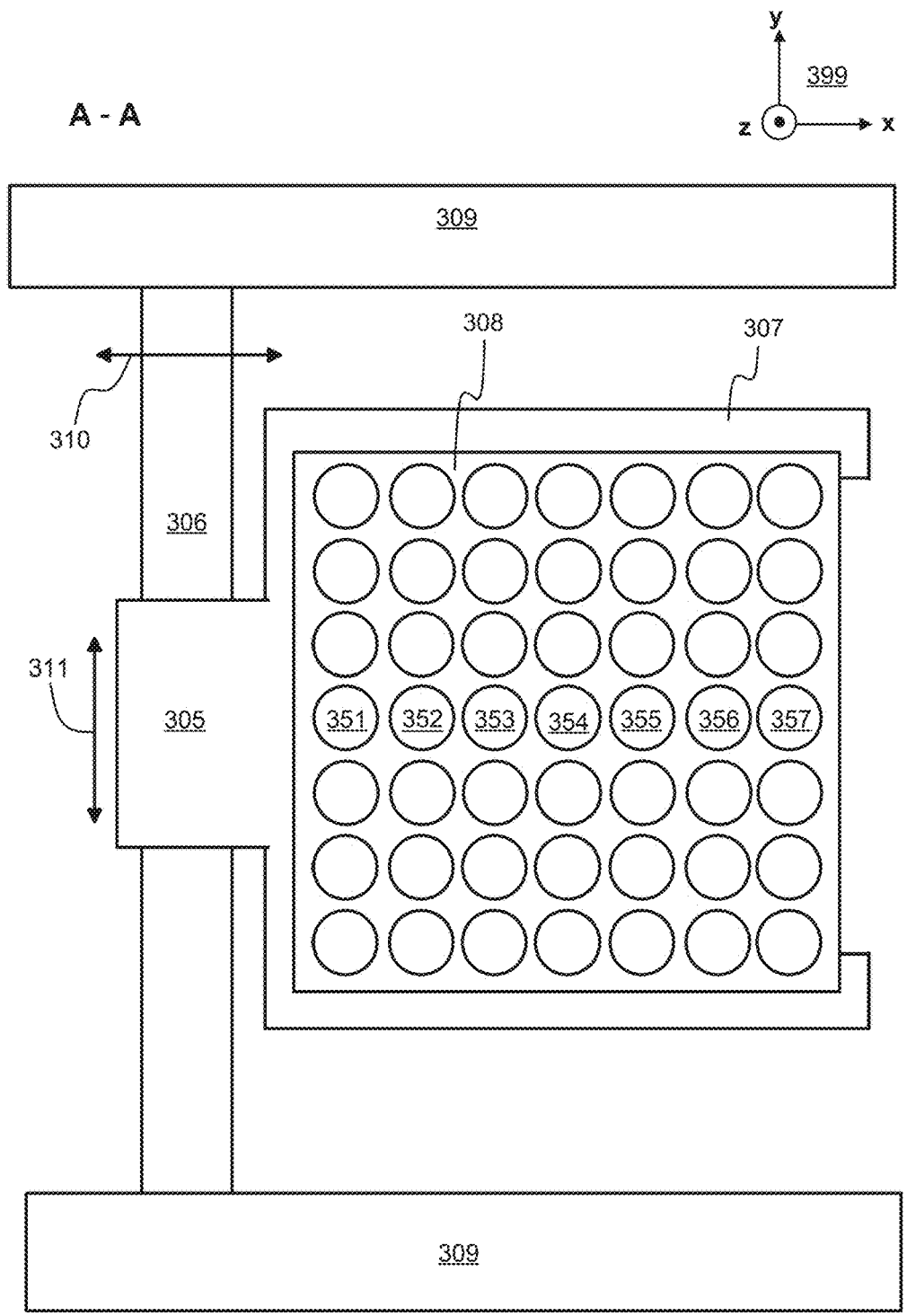

FIG. 3a shows a schematic illustration of an optical measurement instrument according to an exemplifying and non-limiting embodiment. FIG. 3b shows a schematic illustration of a view seen downwards from a line A-A shown in FIG. 3a. The optical measurement instrument comprises mechanical support elements arranged to support a sample plate 308 that can be e.g. a microtitration plate. The sample plate comprises sample wells 351, 352, 353, 354, 355, 356, and 357. In the exemplifying situation shown in FIG. 3a, each of the sample wells 351-357 contains one or more substances capable of emitting fluorescence signal after being excited with excitation radiation, and each of the sample wells 351, 352, 353, and 354 contains a sample of material to be analyzed, e.g. blood, and possibly a portion of a sample carrier. In this exemplifying case, each portion of a sample carrier is a piece cut off from a filter paper or from some other suitable solid material. In FIG. 3a, one of the pieces is denoted with a reference number 360. However, the samples could have been brought to the sample wells with the aid sample carrier liquid as well.

The mechanical support elements arranged to support a sample plate 308 comprise a support rail 306 and guide elements 309 shown in FIG. 3b. The support rail 306 is supported relative to a body of the optical measurement instrument with the aid of the guide elements 309 in such a way that the support rail 306 is movable in the directions of a two-headed arrow 310 shown in FIG. 3b. The mechanical support elements comprise a sledge 307 capable of receiving the sample plate 308. The sledge is connected to the support rail 306 in such a way that the sledge is capable of sliding along the support rail in the longitudinal direction of the support rail, i.e. the sledge is movable with respect to the support rail 306 in the directions of a two-headed arrow 311 shown in FIG. 3b. Therefore, the sample plate 308 is movable in the xy-plane defined by a coordinate system 399. Due to the fact that the sample wells are movable in the xy-plane, the contents of different sample wells can be measured in a temporally successive manner so that each sample well is in turn the sample well whose content is being measured.

The optical measurement instrument comprises an excitation radiation source 303 shown in FIG. 3a, and a light guide 304 for directing excitation radiation to one of the sample wells in turn. In the exemplifying situation shown in FIG. 3a, the sample well 352 is positioned to be capable of receiving the excitation radiation from the light guide 304. The optical measurement equipment comprises a photo-detector 302 for measuring a fluorescence emission signal from one of the sample wells in turn. The photo-detector 302 can be based on for example a photodiode or a photomultiplier tube. The optical measurement instrument comprises a control system 301 for controlling the operation of the excitation radiation source 303 and the photo-detector 302. The excitation radiation source 303, the photo-detector 302, and/or the light guide 304 can be either integral or replaceable components of the optical measurement instrument. The control system 301 can be implemented with one or more programmable processor circuits, one or more dedicated hardware circuits such as an application specific integrated circuit "ASIC", one or more field programmable logic circuits such as a field programmable gate array "FPGA", or a combination of these. Furthermore, the optical measurement instrument may comprise for example an optical filtering device with the aid of which an appropriate wavelength band can be selected for each measurement.

The optical measurement instrument comprises a device according to an exemplifying and non-limiting embodiment for detecting whether a sample well, e.g. the sample well 352, contains a sample and also a possible portion of a sample carrier. The device comprises:

means for computing, on the basis of a fluorescence emission signal measured from the sample well, an indicator value indicative of the decay time of the measured fluorescence emission signal, means for comparing the indicator value to a reference value, and means for setting, in accordance with the comparison between the indicator value and the reference value, a detection result to express one of the following: (i) the sample well contains the sample and the possible portion of the sample carrier, (ii) the sample well does not contain the sample and the possible portion of the sample carrier.

In the optical measurement instrument illustrated in FIGS. 3a and 3b, the control system 301 comprises a controller 312 which is configured to constitute the above-mentioned device for detecting whether the sample well contains the sample and the possible portion of the sample carrier. The controller 312 can be implemented for example with the aid of software means and by using same hardware that is used for implementing at least a part of other functionalities of the optical measurement instrument. It is also possible that the controller 312, or a part of it, has its own hardware. The detection result which expresses whether the sample well under consideration contains the sample and the possible portion of the sample carrier can be used as an input signal for one or more other functionalities of the optical measurement instrument. For example, an alarm signal can be generated and delivered to a user when a sample well which should contain a sample and a possible portion of a sample carrier is detected to be without a sample.

In a device according to an exemplifying and non-limiting embodiment, the controller 312 is configured to read from a memory 313 the above-mentioned reference value which is compared to the indicator value indicative of the decay time.

In a device according to another exemplifying and non-limiting embodiment, the controller 312 is configured to:

compute, on the basis of a fluorescence emission signal measured from a reference sample well lacking a sample, a reference indicator value indicative of the decay time of the fluorescence emission signal measured from the reference sample well, and compute the reference value on the basis of the reference indicator value.

For example, in the situation shown in FIG. 3a, the sample well 357 that does not contain a sample and a portion of a sample carrier can be the above-mentioned reference sample well.

In a device according to an exemplifying and non-limiting embodiment, the controller 312 is configured to:

compute, for each of reference sample wells lacking samples on the basis of fluorescence emission signals measured from the reference sample wells, a reference indicator value indicative of the decay time of the fluorescence emission signal measured from the reference sample well under consideration, compute the reference value on the basis of the reference indicator values computed for the reference sample wells.

For example, in the situation shown in FIG. 3a, the sample wells 354, 356, and 357 that do not contain samples and possible portions of sample carriers can be the above-mentioned reference sample wells.

In a device according to an exemplifying and non-limiting embodiment, the controller 312 is configured to compute the indicator value according to the following formula:

$$\frac{\Delta T}{\ln(C_1) - \ln(C_2)},$$

where $\Delta T$ is a time-shift between starting points of two measurement time windows having equal temporal lengths, $C_1$ is a value proportional to strength of a signal received at the photo-detector 302 when measuring the fluorescence emission signal from the sample well during an earlier one of the measurement time windows, and $C_2$ is a value proportional to strength of a signal received at the photo-detector when measuring the fluorescence emission signal from the sample well during a later one of the measurement time windows.

In a device according to an exemplifying and non-limiting embodiment, the controller 312 is configured to compute preliminary indicator values for mutually different pairs of measurement time windows and compute the indicator value on the basis of the preliminary indicator values.

In a device according to an exemplifying and non-limiting embodiment, the controller 312 is configured to compute the indicator value according to the following formula:

$$\frac{\Delta T}{C_1 - C_2}.$$

In a device according to an exemplifying and non-limiting embodiment, the controller 312 is configured to compute the indicator value according to the following formula:

$$\Delta T \frac{C_2}{C_1}.$$

The specific examples provided in the description given above should not be construed as limiting. Therefore, the protection scope is not limited merely to the exemplifying embodiments described above.

What is claimed is:

1. A device for detecting a sample, the device comprising a controller configured to:

compute, on the basis of a luminescence emission signal measured from a sample well, an indicator value indicative of a decay time of the measured luminescence emission signal, wherein the decay time of the measured luminescence emission signal is different when the sample is present in the sample well than when the sample is absent from the sample well, compare the indicator value to a reference value, and set, in accordance with a comparison between the indicator value and the reference value, a detection result to express one of the following: (i) the sample well contains the sample, (ii) the sample is absent from the sample well.

2. A device according to claim 1, wherein the controller is configured to read the reference value from a memory.

3. A device according to claim 1, wherein the controller is configured to:
compute, on the basis of a luminescence emission signal measured from a reference sample well lacking a sample, a reference indicator value indicative of a decay time of the luminescence emission signal measured from the reference sample well, and
compute the reference value on the basis of the reference indicator value.

4. A device according to claim 1, wherein the controller is configured to:
compute, for each of reference sample wells lacking samples on the basis of luminescence emission signals measured from the reference sample wells, a reference indicator value indicative of a decay time of the luminescence emission signal measured from the reference sample well under consideration,
compute the reference value on the basis of the reference indicator values computed for the reference sample wells.

5. A device according to claim 1, wherein the controller is configured to compute the indicator value according to the formula:

$$\frac{\Delta T}{\ln(C_1) - \ln(C_2)},$$

where ln means the natural logarithm, $\Delta T$ is a time-shift between starting points of two measurement time windows having equal temporal lengths, $C_1$ is a value proportional to strength of a signal received at a photo-detector when measuring the luminescence emission signal from the sample well during an earlier one of the measurement time windows, and $C_2$ is a value proportional to strength of a signal received at the photo-detector when measuring the luminescence emission signal from the sample well during a later one of the measurement time windows.

6. A device according to claim 5, wherein the controller is configured to compute preliminary indicator values for mutually different pairs of measurement time windows and compute the indicator value on the basis of the preliminary indicator values.

7. A device according to claim 1, wherein the controller is configured to compute the indicator value according to the formula:

$$\frac{\Delta T}{C_1 - C_2},$$

where $\Delta T$ is a time-shift between starting points of two measurement time windows having equal temporal lengths, $C_1$ is a value proportional to strength of a signal received at a photo-detector when measuring the luminescence emission signal from the sample well during an earlier one of the measurement time windows, and $C_2$ is a value proportional to strength of a signal received at the photo-detector when measuring the luminescence emission signal from the sample well during a later one of the measurement time windows.

8. A device according to claim 1, wherein the controller is configured to compute the indicator value according to the formula:

$$\Delta T \frac{C_2}{C_1},$$

where $\Delta T$ is a time-shift between starting points of two measurement time windows having equal temporal lengths, $C_1$ is a value proportional to strength of a signal received at a photo-detector when measuring the luminescence emission signal from the sample well during an earlier one of the measurement time windows, and $C_2$ is a value proportional to strength of a signal received at the photo-detector when measuring the luminescence emission signal from the sample well during a later one of the measurement time windows.

9. An optical measurement instrument comprising:
a photo-detector for measuring luminescence emission signal from a sample well, and
a control system for controlling operation of the photo detector,
wherein the control system is configured to constitute a device for detecting whether the sample well contains a sample, the device comprising a controller configured to:
compute, on the basis of the luminescence emission signal measured from the sample well, an indicator value indicative of a decay time of the measured luminescence emission signal, wherein the decay time of the measured luminescence emission signal is different when the sample is present in the sample well than when the sample is absent from the sample well,
compare the indicator value to a reference value, and
set, in accordance with a comparison between the indicator value and the reference value, a detection result to express one of the following: (i) the sample well contains the sample, (ii) the sample is absent from the sample well.

10. A method for detecting a sample, the method comprising:
computing, on the basis of a luminescence emission signal measured from a sample well, an indicator value indicative of a decay time of the measured luminescence emission signal, wherein the decay time of the measured luminescence emission signal is different when the sample is present in the sample well than when the sample is absent from the sample well,
comparing the indicator value to a reference value, and
setting, in accordance with a comparison between the indicator value and the reference value, a detection result to express one of the following: (i) the sample well contains the sample, (ii) the sample is absent from the sample well.

11. A method according to claim 10, wherein the method comprises reading the reference value from a memory.

12. A method according to claim 10, wherein the method comprises:
computing, on the basis of a luminescence emission signal measured from a reference sample well lacking a sample, a reference indicator value indicative of a decay time of the luminescence emission signal measured from the reference sample well, and
computing the reference value on the basis of the reference indicator value.

13. A method according to claim 10, wherein the method comprises:
computing, for each of reference sample wells lacking samples on the basis of luminescence emission signals measured from the reference sample wells, a reference indicator value indicative of a decay time of the luminescence emission signal measured from the reference sample well under consideration, computing the reference value on the basis of the reference indicator values computed for the reference sample wells.

14. A method according to claim 10, wherein the method comprises computing the indicator value according to the formula:

$$\frac{\Delta T}{\ln(C_1) - \ln(C_2)},$$

where ln means the natural logarithm, $\Delta T$ is a time-shift between starting points of two measurement time windows having equal temporal lengths, $C_1$ is a value proportional to strength of a signal received at a photo-detector when measuring the luminescence emission signal from the sample well during an earlier one of the measurement time windows, and $C_2$ is a value proportional to strength of a signal received at the photo-detector when measuring the luminescence emission signal from the sample well during a later one of the measurement time windows.

15. A method according to claim 14, wherein the method comprises computing preliminary indicator values for mutually different pairs of measurement time windows and computing the indicator value on the basis of the preliminary indicator values.

16. A method according to claim 10, wherein the method comprises computing the indicator value according to the formula:

$$\frac{\Delta T}{C_1 - C_2},$$

where $\Delta T$ is a time-shift between starting points of two measurement time windows having equal temporal lengths, $C_1$ is a value proportional to strength of a signal received at a photo-detector when measuring the luminescence emission signal from the sample well during an earlier one of the measurement time windows, and $C_2$ is a value proportional to strength of a signal received at the photo-detector when measuring the luminescence emission signal from the sample well during a later one of the measurement time windows.

17. A method according to claim 10, wherein the method comprises computing the indicator value according to the formula:

$$\Delta T \frac{C_2}{C_1},$$

where $\Delta T$ is a time-shift between starting points of two measurement time windows having equal temporal lengths, $C_1$ is a value proportional to strength of a signal received at a photo-detector when measuring the luminescence emission signal from the sample well during an earlier one of the measurement time windows, and $C_2$ is a value proportional to strength of a signal received at the photo-detector when measuring the luminescence emission signal from the sample well during a later one of the measurement time windows.

18. A non-transitory computer readable medium encoded with a computer program for detecting a sample, the computer program comprising computer executable instructions for controlling a programmable processing system to:

compute, on the basis of a luminescence emission signal measured from a sample well, an indicator value indicative of a decay time of the measured luminescence emission signal, wherein the decay time of the measured luminescence emission signal is different when the sample is present in the sample well than when the sample is absent from the sample well, compare the indicator value to a reference value, and set, in accordance with a comparison between the indicator value and the reference value, a detection result to express one of the following: (i) the sample well contains the sample, (ii) the sample is absent from the sample well.

* * * * *